US006569332B2

(12) United States Patent
Ainsworth et al.

(10) Patent No.: US 6,569,332 B2
(45) Date of Patent: *May 27, 2003

(54) INTEGRATED ANAEROBIC DIGESTER SYSTEM

(76) Inventors: Jack L. Ainsworth, 2419 VZ CR 2318, Canton, TX (US) 75103; Dan Atwood, 2746 Lighthouse Dr., Nassau Bay, TX (US) 77058; Tom Rideout, 4106 S. CR 1185, Midland, TX (US) 79706

( * ) Notice: Subject to any disclaimer, the term of this patent is extended or adjusted under 35 U.S.C. 154(b) by 0 days.

This patent is subject to a terminal disclaimer.

(21) Appl. No.: 09/963,130

(22) Filed: Sep. 24, 2001

(65) Prior Publication Data

US 2002/0079266 A1 Jun. 27, 2002

Related U.S. Application Data

(63) Continuation-in-part of application No. 09/602,684, filed on Jun. 26, 2000, now Pat. No. 6,299,774.

(51) Int. Cl.[7] .............................. C02F 3/28; C02F 3/34; C05F 1/00; C05F 3/02; C05F 15/00
(52) U.S. Cl. ...................... 210/603; 210/612; 210/613; 210/632; 210/178; 210/180; 210/205; 210/218; 210/221.2; 435/262.5; 435/290.2; 71/10; 71/15; 71/16; 71/19; 71/21; 71/23
(58) Field of Search ................................ 210/603, 605, 210/612, 613, 632, 178, 179–180, 198.1, 205, 218, 220, 221.1, 221.2; 435/262, 262.5, 290.1, 290.2; 71/10–24

(56) References Cited

U.S. PATENT DOCUMENTS 3,959,125 A      5/1976 Teltzke
3,981,800 A  *  9/1976 Ort .............................. 210/603
4,100,023 A  *  7/1978 McDonald .................. 435/167
4,198,211 A  *  4/1980 Shattock ..................... 48/197 A
4,298,621 A  * 11/1981 Samis et al. .................. 426/55
4,321,141 A  *  3/1982 Messing ...................... 210/603
4,354,936 A  * 10/1982 Ishida et al. ................ 210/602
4,372,856 A  *  2/1983 Morrison .................... 210/603
4,565,552 A      1/1986 Cotton
4,599,167 A  *  7/1986 Benjes et al. ............... 210/150
4,696,746 A  *  9/1987 Ghosh et al. ............... 210/603
5,180,494 A  *  1/1993 Yamaguchi et al. ........ 210/603
5,338,452 A  *  8/1994 Pidaparti ..................... 210/603
5,447,850 A  *  9/1995 McCann ....................... 435/42
6,019,900 A  *  2/2000 Brink et al. ................ 210/603
6,296,766 B1 * 10/2001 Breckenridge .............. 210/613
6,299,774 B1 * 10/2001 Ainsworth et al. ......... 210/120
6,383,371 B1 *  5/2002 Ripley ......................... 435/167
6,410,283 B1 *  6/2002 Rehmat et al. ............. 435/167

* cited by examiner

Primary Examiner—Fred Prince
(74) Attorney, Agent, or Firm—Rick Matos; Innovar, L.L.C.

(57) ABSTRACT

A process to recover energy, reduce pollution potential, and add value to organic waste such as animal manure is described. The process involves the anaerobic digestion of feedstocks, such as animal manure, at low to high temperatures in batch, semi-continuous or continuous reactors. The process makes use of existing handling and storage equipment at the farm and requires minimal supervision and skill by the operator. The system is not affected by high concentrations of volatile acids and ammonia or nitrogen. The productivity of the anaerobic digester system, in terms of methane gas production and quality, is exceptionally high. The anaerobic digester employs plural pressurizable anaerobic digesters connected in parallel. Consequently, the process is scaleable, low cost and does not interfere with regular farm operations.

79 Claims, 5 Drawing Sheets

INTEGRATED ANAEROBIC DIGESTER SYSTEM

CROSS-REFERENCE TO EARLIER FILED APPLICATION

The present application is a continuation-in-part of U.S. application Ser. No. 09/602,684 filed Jun. 26, 2000, which is now U.S. Pat. No. 6,299,774.

FIELD OF THE INVENTION

The present invention relates generally to an improved process and equipment for converting feedstock into useful materials, and more specifically, to an anaerobic fermentative process for bioconverting animal waste, sewage sludge or other biodegradable feedstock into methane gas, carbon dioxide gas, ammonia, carbon black, organic acid, charcoal, a fertilizer and/or an insecticidal mixture.

BACKGROUND OF THE INVENTION

Animal waste poses a significant problem in the poultry, swine and cattle industries. Animal waste from animal raising or processing operations is responsible for a significant amount of underground water contamination and methods are continually being developed for handling animal wastes. One known method is the bioconversion of animal waste into useful products.

Methods for the anaerobic digestion or treatment of sludge, animal waste, synthesis gas or cellulose-containing waste are disclosed in U.S. Pat. Nos. 5,906,931 to Nilsson et al., No. 5,863,434 to Masse et al., No. 5,821,111 to Grady et al. No. 5,746,919 to Dague et al., No. 5,709,796 to Fuqua et al., No. 5,626,755 to Keyser et al., No. 5,567,325 to Townsley et al., No. 5,525,229 to Shih, No. 5,464,766 to Bruno, No. 5,143,835 to Nakatsugawa et al., No. 4,735,724 to Chynoweth, No. 4,676,906 to Crawford et al., No. 4,529,513 to McLennan, No. 4,503,154 to Paton, No. 4,372,856 to Morrison, No. 4,157,958 to Chow, and No. 4,067,801 to Ishida et al. These patents disclose different processes and equipment for the bioconversion, either by microbial digestion or enzymatic conversion, of those materials into methane and other useful materials.

The equipment used for the anaerobic digestion or fermentation of waste into fuel, such as methane, varies greatly and is generally tailored to specific applications. Equipment that is suitable for a first type of feedstock generally has to be modified before it can be used for a second different type of feedstock.

Chemical and biochemical reactions that create a gas are generally conducted at low to sub-atmospheric pressures due to the tendency of the product gas to function as feedback inhibitor that inhibits further formation of the gas. The art recognizes that variations in the pressure of an anaerobic digester can be used to effect different biochemical and productivity results. U.S. Pat. No. 4,409,102 to Tanner discloses an anaerobic digestion conducted at sub-atmospheric pressures that unexpectedly affect an increase in methane gas production. U.S. Pat. No. 3,994,780 to Klass et al. discloses the high pressure rupture of cells in an anaerobic digester to render cellular components available to other intact cells in the digester. U.S. Pat. No. 3,981,800 to Ort discloses a process for preparing high quality methane (about 98% wt.) with an anaerobic digester operated at 1–5 atm. above atmospheric pressure provided that the sludge is degassed by a recirculator and passed between two digesters connected serially to remove carbon dioxide in the sludge that is then fed back into the digester. Therefore, unlike the presently claimed system, the system or Ort requires that each batch of feedstock under go a two-stage digestion, wherein the feedstock is predigested in a first anaerobic digester and then completely digested in a second anaerobic digester that is connected serially with the first anaerobic digester. U.S. Pat. No. 4,100,023 to McDonald discloses that the internal pressure of the anaerobic digester should be kept at about 1 to 3 inches of water column to ensure proper performance. U.S. Pat. No. 4,568,457 to Sullivan discloses a two-stage anaerobic digester system having an acid forming stage and a methane gas forming stage, wherein the pressure of the gas in the headspace of the two stages can be slightly above atmospheric pressure.

Methanogenic microbes that create methane from carbon and hydrogen containing feedstocks, such as cellulose, animal waste, food processing waste, and sludge, are well known. These microbes have been used in the waste processing industry and are available in their native forms from natural sources or in genetically altered or manipulated forms, which can produce greater amounts of useful materials per unit weight of waste than can unaltered methanogenic bacteria.

To date, no equipment containing the required components as described herein has been disclosed. Further, the improved equipment design and layout of the present invention provides a higher yield of methane and other useful materials than other comparable equipment. Still further, the improved process and equipment of the invention can be used in the poultry, swine, dairy or cattle industries to convert cellulose-containing animal waste into methane which is used to operate farm or ranch equipment thereby reducing operating costs and the volume of waste produced.

SUMMARY OF THE INVENTION

The present invention provides a system for converting cellulose-containing feedstock into useful materials, wherein the system comprises:

a feedstock slurry feeder;

a plurality of conduits connecting various components of the system;

a single pressurizable anaerobic digester comprising agitation means, one or more feed ports, one or more discharge ports, an optional pressure regulator, and a reaction vessel for holding a reaction solution comprising an anaerobic microbe which converts an aqueous slurry of cellulose-containing feedstock into at least methane and an enriched effluent;

a pressurizer; and one or more gas processors directly or indirectly connected to the anaerobic digester;

wherein the headspace of the anaerobic digester is pressurized to about 10 psi or more to form the enriched effluent and a discharge gas comprising at least methane during anaerobic digestion of the feedstock slurry.

Depending on the feedstock slurry used, the anaerobic digester will also form a fertilizer, sludge, scum, ammonia, charcoal, carbon black, an organic acid and/or an insecticidal mixture. The anaerobic digester is preferably operated at pressures between 10 to 265 psi, more preferably 10 to 100 psi, and even more preferably 25–75 psi. In preferred embodiments, the system also comprises one or more of the following: one or more gas scrubbers, one or more heaters for heating or preheating the slurry being digested in the anaerobic digester, one or more water storage tanks, one or more feedstock slurry tanks, one or more feedstock grinders, one or more supernatant storage tanks, one or more sludge storage tanks, one or more sludge dryers, one or more scum storage tanks, one or more $CO_2$ tanks, and/or one or more produced gas storage tanks.

Other preferred embodiments include those wherein the system does not require a water lagoon, a foam trap, and/or a water vapor trap. Still other preferred embodiments include those wherein: (1) the system is operated in a batch, semi-continuous, or continuous mode; (2) the feedstock slurry comprises from about 1–90% wt. solids, more preferably about 1–60% wt. solids, or even more preferably about 1–40% wt. solids; (3) the agitation means comprises a gas bubbler, an aerator, a sparger bar, a fluid stream, a mechanical agitator, or a combination thereof; (4) the feedstock slurry is gravity fed or fed under pressure to the anaerobic digester; (5) the pressurizer pressurizes the anaerobic digester with gas or a liquid; (6) the pressurizer is the feedstock slurry feeder, which is preferably a pump, gravity feed system, or a gas compressor; (7) the anaerobic digester does not require aerobic digestion of the feedstock; (8) the anaerobic digester does not require multiple discrete zones of environmentally incompatible waste-digestive microorganisms; (9) the anaerobic microbe is a methanogenic bacterium; (10) the anaerobic microbe is mesophilic or thermophilic; (11) methane produced by the anaerobic digester is used to operate an internal combustion engine, an electrical current generator, an electric engine, a water heater, a furnace, an air conditioning unit, a ventilation fan, a conveyor, a pump, a heat exchanger, fuel cell, or various components of the system itself and/or to recharge power cells; (12) the gas processor comprises a gas scrubber and/or a gas separator; (13) a gas recirculator is used to recirculate gas from the headspace of the reactor to the slurry in the reactor; (14) a gas recirculator adds methane-depleted or carbon dioxide enriched biogas back to the reactor; and/or (15) a fluid recirculator recycles the scum, supernatant, effluent, or sludge of the reactor.

Another aspect of the invention provides a system for converting cellulose-containing feedstock into useful materials, wherein the system comprises:
one or more feedstock slurry feeders;
two or more pressurizable anaerobic digesters connected in parallel, each anaerobic digester comprising agitation means, one or more feed ports, one or more discharge ports, an optional pressure regulator, and a reaction vessel for holding a reaction solution comprising an anaerobic microbe which converts an aqueous slurry of cellulose-containing feedstock into at least methane and an enriched effluent;
one or more pressurizers;
one or more gas processors directly or indirectly connected to each anaerobic digester; and
a plurality of conduits connecting various components of the system;
wherein the headspace of each anaerobic digester is pressurizable to about 10 psi or more to form the enriched effluent and a discharge gas comprising at least methane during anaerobic digestion of the feedstock slurry.

Specific embodiments of this aspect of the invention include those wherein: 1) a major portion of the discharge gas is methane; 2) the system comprises a single feedstock slurry feeder connected to each of two or more pressurizable anaerobic digesters connected in parallel; 3) the enriched effluent from a first pressurizable anaerobic digester is not fed into a second pressurizable anaerobic digester; 4) the system further comprises one or more receiving tanks that receive the enriched effluent from each pressurizable anaerobic digester.

Another aspect of the invention provides an integrated system for converting cellulose-containing feedstock into useful materials, wherein the integrated system comprises:
a feedstock slurry feeder system that forms an aqueous slurry of cellulose-containing feedstock;
an anaerobic digester system directly or indirectly connected to the feeder system and comprising two or more pressurizable anaerobic digesters connected in parallel, wherein each anaerobic digester receives the aqueous slurry of cellulose-containing feedstock and converts it into a discharge gas and an enriched effluent; and
a discharge gas processing system that is directly or indirectly connected to the anaerobic digester system and that at least separates methane from the discharge gas;
wherein the headspace of each anaerobic digester is pressurizable to about 10 psi or more to form the enriched effluent and a discharge gas comprising at least methane during anaerobic digestion of the feedstock slurry.

Specific embodiments include those wherein: 1) the integrated system further comprises an enriched effluent processing system; 2) the integrated system further comprises a pressurizer system; 3) the feedstock slurry feeder system comprises one or more mixing vessels and one or more pumps; 4) the discharge gas processing system comprises a dehydrator, separator, and scrubber; 5) each anaerobic digester comprises agitation means, one or more feed ports, one or more discharge ports, an optional pressure regulator, and a reaction vessel for holding a reaction solution comprising an anaerobic microbe that converts the aqueous slurry of cellulose-containing feedstock into at least methane and the enriched effluent; 6) the discharge gas processing system comprises one or more separators for separating $CO_2$ or ammonia gas from the discharge gas; 7) the integrated system further comprises a gas recirculator to recirculate gas from the headspace of an anaerobic digester to the slurry of the digester; 8) a gas recirculator adds methane-depleted or carbon dioxide enriched discharge gas back to an anaerobic digester; and/or 9) the integrated system further comprises a fluid recirculator system that recycles the scum, supernatant, effluent, or sludge of an anaerobic digester.

Another aspect of the invention provides an integrated anaerobic digester system comprising:
a single-stage anaerobic digester system comprising two or more pressurizable anaerobic digesters connected in parallel, wherein each anaerobic digester receives an aqueous slurry of cellulose-containing feedstock and converts it into a discharge gas and an enriched effluent;
a discharge gas processing system that is directly or indirectly connected to the anaerobic digester system and that at least separates methane from the discharge gas; and
an enriched effluent processing system that is directly or indirectly connected to the anaerobic digester system;
wherein the headspace of each anaerobic digester is pressurizable to about 10 psi or more to form the enriched effluent and a discharge gas comprising at least methane during anaerobic digestion of the aqueous slurry of cellulose-containing feedstock.

Other features, advantages and embodiments of the invention will be apparent to those skilled in the art by the following description, accompanying examples and appended claims.

BRIEF DESCRIPTION OF THE DRAWINGS

The following drawings are part of the present specification and are included to further demonstrate certain aspects of the invention. The invention may be better understood by reference to one or more of these drawings in combination with the detailed description of the specific embodiments presented herein.

DETAILED DESCRIPTION OF THE INVENTION

Figure 1A:
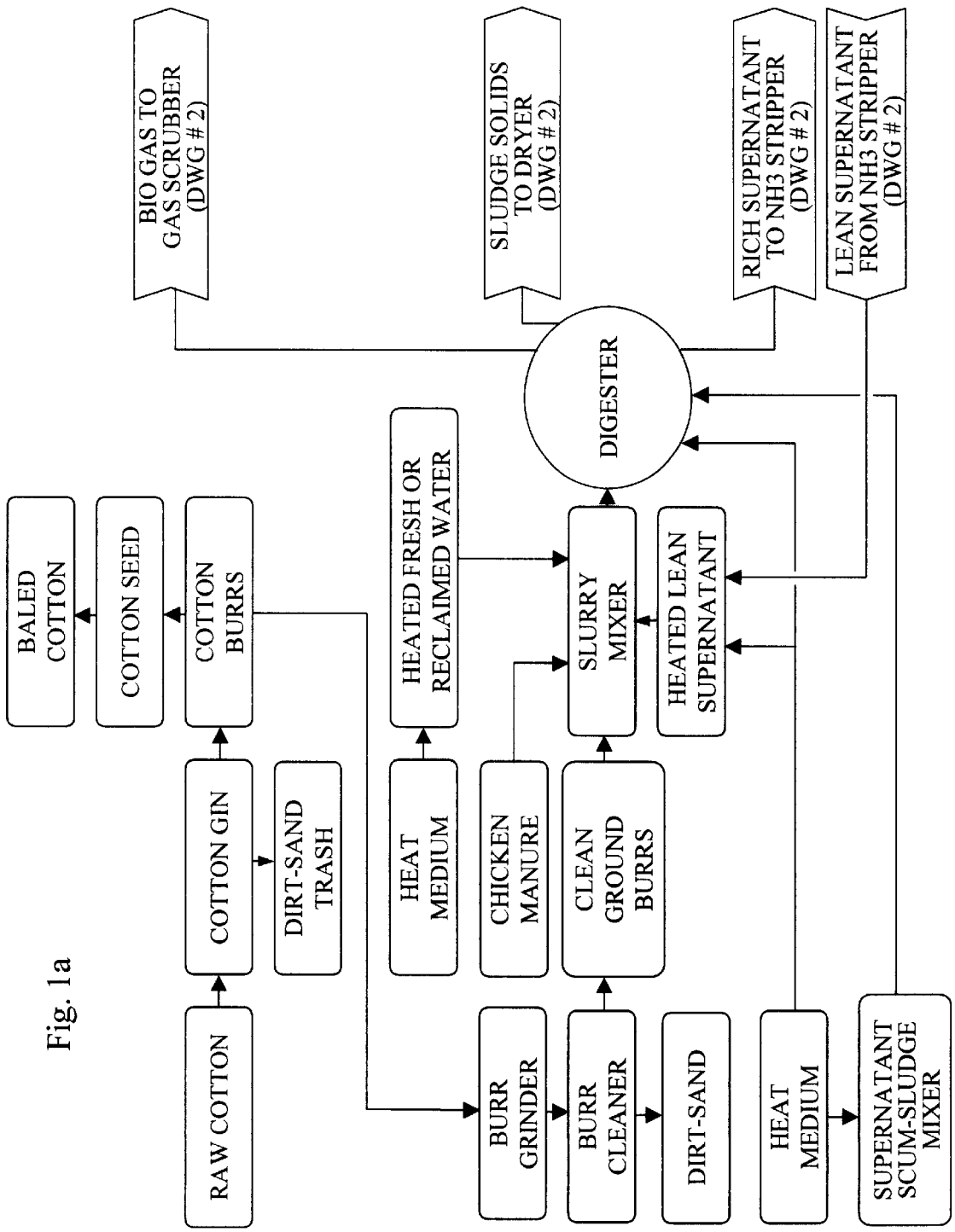
FIGS. 1a and 1b are process flow schematics of a first preferred embodiment of the anaerobic digester system according to the invention.

The present invention is different than known anaerobic digester system primarily in that it is conducted at elevated pressures of at least about 10 psi up to about 265 psi, more preferably 10 to 100 psi, and even more preferably 25–75 psi, during anaerobic digestion of a feedstock slurry and the system requires only a single stage of anaerobic digestion. The anaerobic digester system also includes an advantageous combination of known and unknown features that unexpectedly provides a very efficient system for converting biomass into methane gas, a nutrient enriched solution, and optionally an insecticidal mixture.

As used herein, the phrase "single stage of anaerobic digestion" is taken to mean that anaerobic digestion of the aqueous feedstock slurry is accomplished by placing a charge of an aqueous feedstock slurry into a pressurizable anaerobic digester until sufficiently digested and passing the formed gas onto the discharge gas processing system and the remaining fluid (liquid/solids) onto the enriched effluent processing system such that a partially charge of feedstock is not passed from a first anaerobic digester to a second anaerobic digester. Accordingly, a single-stage anaerobic digester system can have one or two or more anaerobic digesters connected in parallel but not in series. A parallel anaerobic digester system is unlike the serial anaerobic digester system of Ort, wherein the charge from a first anaerobic digester is passed onto a second anaerobic digester before it is passed onto the enriched effluent processing system. A serial anaerobic digester system is a two-stage or multi-stage system, whereas the system of the present invention is a single-stage anaerobic digester system.

As used herein, the term "feedstock" is taken to mean any animal or plant derived material that contains one or more components that can be converted, bioconverted or biodegraded into a useful material by the anaerobic digester of the invention. Animal tissue, biomass, fish tissue or parts, plant parts, fruits, vegetables, plant processing waste, animal processing waste, animal manure or urine, mammalian manure or urine solids isolated from fermentation cultures, and combinations thereof are included in the term feedstock. Particular examples of feedstock include bovine, poultry, equine or porcine manure or urine, wood shavings or chips, slops, mostos, shredded paper, cotton burrs, grain, chaff, seed shells, hay, alfalfa, grass, leaves, sea shells, seed pods, corn shucks, weeds, aquatic plants, algae and fungus and combinations thereof. Combinations of poultry, bovine, equine or porcine urine and/or manure with wood shavings, wood chips, shredded paper, cotton burrs, seed shells, hay, alfalfa, grass, leaves, seed pods, or corn shucks are particularly preferred and are generally referred to as cellulose-containing feedstock.

A feedstock slurry is prepared by suspending a feedstock in an aqueous solution to form a slurry comprising less than about 90% wt. solids, preferably about 0.1–60% wt. solids, or even more preferably about 1–40% wt. solids. The particle size of the feedstock can be reduced either prior to or during preparation of the feedstock slurry by employing an in-line or immersed abrader, classifier, mill, high shear mixer, grinder, homogenizer or other particle size reducer known to those of ordinary skill in the art. No particular particle size is required for the feedstock; however, smaller particle sizes are preferred as smaller particles are generally bioconverted more quickly than larger particles.

Grit, such as dirt, sand, soil, stones, pebbles, rocks, feathers, hair and other such materials, is preferably removed prior to addition of the feedstock slurry to the anaerobic digester; however, grit can be removed at any point along the process. Equipment such as classifiers, settling tanks, multiphase tanks, and/or or filters can be used to remove the grit.

As used herein, the term "useful material" is taken to mean methane gas; hydrogen gas; carbon dioxide; hydrogen sulfide; nitrogen rich fertilizer; protein, amino acid, carbohydrate and/or mineral rich solution or slurry; insecticidal mixture; charcoal; carbon black; insect repellant mixture; combinations thereof and other such materials which can be prepared by anaerobic digesters from a feedstock. Methane, a nitrogen rich fertilizer, charcoal and an insecticidal slurry are particularly preferred useful materials.

The anaerobic microbe used in the anaerobic digester is any anaerobic bacterium, fungus, mold or alga, or progeny thereof, which is capable of converting the feedstock to a useful material in the anaerobic digester of the invention. Preferred anaerobic microbes are isolated from decaying or composted feedstock, are endogenous to the area in which the feedstock was first obtained, are obtained from bacterial or fungal collections such as those of the American Type Culture Collection (ATCC) or have been genetically altered or engineered to convert a feedstock to a useful material. Particularly preferred anaerobic microbes are those that will convert a cellulose-containing feedstock into methane, a nitrogen rich fertilizer, charcoal, humus and an insecticidal slurry. The anaerobic microbe can be a psychrophile, mesophile or thermophile. Generally, a mesophile will prefer operating temperatures in the range of about 60°–120° F., and a thermophile will prefer operating temperatures in the range of about 120°–160° F.

Examples of an anaerobic microbe which is useful in the anaerobic digester of the invention include yeast, a methanogenic bacterium, methanobacterium, acetobacterium, acetogenic bacterium, liquefaction bacterium, Clostridium spp. (methane), Bacillus spp., Escherichia spp., Staphylococcus spp., Methanobacter spp., *Methanobacter (Mb.) omlianskii* (methane), *Mb. formicicum* (methane), *Mb. soehngenii* (methane), *Mb. thermoautrophicum* (methane), *Mb.*

*ruminatium* (methane), *Mb. mobile* (methane), *Mb. methanica* (methane), *Methanococcus* (*Mc.*) *mazei* (methane), *Mc. vannielii* (methane), *Ms. mazei* (methane), *Mb. suboxydans* (methane), *Mb. propionicum* (methane), *Methanosarcina* (*Ms.*) *bovekeri* (methane), *Ms. methanica* (methane), *Ms. alcaliphilum* (methane), *Ms. acetivorans* (methane), *Ms. thermophilia* (methane), *Ms. barkeri* (methane), *Ms. vacuolata* (methane), *Propionibacterium acidi-propionici* (methane), *Saccharomyces cerevisae* (ethanol), *S. ellipsoideus* (ethanol), *Clostridium propionicum* (propanol), *Clostridium saccharoacetoper-butylicum* (butanol), *Clostridium butyricum* (hydrogen), wherein the chemical in parentheses indicates a useful material which that microbe produces.

Other microbes and/or enzymatic catalysts can be added to the anaerobic digester to facilitate breakdown of the feedstock into components which are usable by the anaerobic microbe as either nutrients or starting materials for useful materials made by the anaerobic microbe. Such other microbes and/or enzymes include, for example, amylases, proteases, cellulases, hydrolases, lipid hydrolyzing enzymes, lysozymes, phosphatases, esterases, amidases, and lipases.

The conditions inside the anaerobic digester will vary according to the useful material being produced, the anaerobic microbe being used, the configuration of the anaerobic digester, the feedstock being converted, the desired productivity of the anaerobic digester, and the form of microbe (immobilized or free-flowing) used. Immobilized microbes can be prepared using any methods known by the artisan of ordinary in the arts. The conditions used to culture the anaerobic microbe and maintain it viable in the anaerobic digester can be varied. Conditions which can be controlled include solids content, reaction solution composition, temperature, gas content, digestion rate, anaerobic microbe content, agitation, feed and effluent rates, gas production rate, carbon/nitrogen ratio of the feedstock, pressure, pH, and retention time in the digester, among other things.

The amount of solids in the digester will generally range from about 1 to about 60% wt., preferably from about 20 to about 50% wt., or more preferably from about 40 to 50% wt. based upon the total solution weight.

The particle size of solids in the digester affects the rate of digestion. Generally, the smaller the particle size, the faster the rate of digestion.

The temperature of the reaction solution is generally in the range of about 60° F. to about 160° F., about 90° F. to about 118° F., about 90° F. to about 115° F., about 90° F. to about 110° F., or about 90°–95° F. The optimum operating temperature will depend upon the anaerobic microbe used, the product being produced, the pressure under which the digestion is conducted, the carbon to nitrogen ratio of the feedstock, and/or the contents of the feedstock. For *Clostridium* spp., the preferred temperature is in the range of about 70°–100° F., about 70°–95° F., or about 75–95° F. For a mesophilic microbe, the highest level of productivity and highest purity methane is generally attained at a temperature in the range of about 90°–118° F.

When the digester is operated as described herein, the type of product gas formed will depend upon the operating pressure of the digester and the components of the discharge gas treatment system used to process and purify the gas. The digester system can be made to produce predominantly methane or carbon dioxide. Higher pressure generally promotes the conversion of carbon dioxide to methane and leads to the formation of high purity methane; therefore, lower pressure generally leads to the formation of more carbon dioxide and less methane. Accordingly, when the optimal operating temperature for a particular combination of anaerobic microbe and feedstock slurry components is identified, the composition of the biogas produced can be altered by changing the pressure at which the digestion is conducted.

The feed rate of the anaerobic digester is expressed in terms of lbs. of feedstock slurry added to the digester per unit time. The feed rate can be varied as desired; however, for a 1000 gal reactor maintained at approximately 80% of capacity, operated at a temperature of about 95°–105° F., and being used to produce methane, about 50 to about 55 lbs. of poultry waste, containing 25% wt. poultry manure and 75% wt. cotton burrs, about $\frac{1}{40}$ of the total weight per hour can be added to the digester.

While not absolutely necessary, the feedstock slurry is generally warmed to a temperature approximating the temperature at which the digester is being operated thereby minimizing temperature fluctuations in the digester that might affect the productivity or efficiency of the system.

The effluent rate, i.e., the rate at which effluent is drawn from the digester, is related to the feed rate of the digester. Generally, the effluent rate will not exceed the feed rate when the digester is operated in a continuous mode. However, the feed rate and effluent rate are generally independent of one another when the digester is operated in a batch or semi-continuous mode. During continuous operation, the slurry level in the digester will preferably remain relatively constant and the feed rate and effluent rate will be kept controlled so as to provide the desired overall residence time in the anaerobic digester. Further, the total amount of feedstock slurry added to the digester will generally exceed the total amount of effluent withdrawn from the digester, since part of the feedstock is converted to a gas that is also drawn from the digester. During continuous operation, feedstock is continuously added to the reactor at approximately the same time that gas, effluent, scum, supernatant and/or sludge are removed from the reactor. During semi-continuous operation, feedstock is added to the reactor incrementally and gas, effluent, scum, supernatant and/or sludge are removed incrementally at the same or different times. It is generally preferred that addition of feedstock slurry and removal of digested slurry occur simultaneously, in an overlapping manner or within a short period of time from one another. During batch operation, larger portions of feedstock are added to the reactor at given time intervals and larger portions of gas, sludge, effluent, supernatant and/or sludge are removed from the reactor at the same or different time intervals. During continuous operation, the operating temperature and rate of gas production will be relatively constant. Generally continuous operation will provide a greater rate of gas production than batch or semi-continuous operation.

Gas production rate is expressed in terms of volume of fuel gas produced per given time interval of operation, e.g. ft.$^3$ of fuel gas produced per hour or day of operation, in terms of volume of fuel gas produced per unit weight of feedstock added to the reactor. In the example described herein, the digester produced approximately 5–8 ft.$^3$ of methane per pound of feedstock.

The quality of the fuel gas produced is generally expressed in terms of the BTU rating of the gas as it is removed from the reactor. In the example described herein, the methane collected from the digester had an average rating of about 500–800 BTU without a recirculation loop installed. Higher ratings in the range of about 800 to about 1000 BTU can be achieved using one or more of the preferred embodiments described herein. Pure methane, or sweet dry methane, has a rating of 1000 BTU.

A gas, such as methane, carbon dioxide, hydrogen, ammonia or hydrogen sulfide, which is produced in the anaerobic digester will be present in the reaction solution and headspace above the reaction solution. The content of each gas in the headspace and the reaction solution will vary according to the conditions, feedstock and/or anaerobic microbe present within the anaerobic digester. The content or percentage of each gas can be monitored using a gas chromatograph or other gas sensing or analyzing equipment used to determine the composition or presence of gases or gaseous mixtures. In preferred embodiments for producing methane, the content of the gas in the headspace will be about 60–100% methane, 0–40% carbon dioxide and 0–10% of other gases, such as ammonia, hydrogen or hydrogen sulfide. Since the digester is operated under approximately or strictly anaerobic conditions, the content of oxygen in the digester will generally be less than about 5%, less than about 1% or about 0%. When methane production starts, the content of oxygen in the digester will be about 0%. In order to minimize the introduction of oxygen into the digester, the feedstock slurry may be degassed before or after loading into the digester. Partial degassing can be done by exposing the feedstock slurry to a vacuum or by equilibrating (purging) it with an inert gas. The feedstock slurry will preferably include little to no oxygen, although it can include other gases.

The methane, carbon dioxide, or hydrogen produced by the anaerobic digester will generally be cleaned or purified by a scrubber to remove moisture, vapor, droplets, suspended solids or other such contaminants. The scrubber can comprise one or more of a filter, desiccant, zeolite, activated carbon, fiber, countercurrent wash solution, mixer, homogenizer, or other such components typically used in association with or comprised within gas scrubbers. Such components are well known to those of ordinary skill in the art of gas processing. In general, hydrogen sulfide is an undesired by-product or off-gas, which is removed from the desired product gas.

The gases that exit the anaerobic digester or the scrubber are then optionally separated into their individual components using conventional gas separation equipment, which is known to those of ordinary skill in the art for separating gas mixtures. The gases may also be processed with one or more compressor, or dehydration equipment. Alternatively, the gases are stored in pressurized storage vessels or tanks once they have been scrubbed. If the stored gas is purified methane or hydrogen or mixtures of methane and hydrogen with carbon dioxide, it can be used directly to operate the anaerobic digester or one or more of its components or it can be used to operate additional equipment such as that described above. Ammonia may also be found in the above-described gases.

The agitation means will agitate the reaction solution in the reaction vessel. Exemplary agitation means include one or more sparger bars, one or more mechanical agitators, a fluid recirculator, a gas recirculator and combinations thereof.

The sparger bar will bubble a gas through the reaction solution. The gas is generally $CO_2$, that is produced by the anaerobic digester system, and can also be an inert gas such as nitrogen. The gas source can be the gas in the headspace of the anaerobic digester, gas that is downstream from the anaerobic digester, or a gas cylinder. A preferred sparger bar will recirculate downstream gas, and preferably gas that has had at least some of its methane removed therefrom, back into the reaction vessel. By feeding back into the reaction solution, in particular the sludge layer thereof, a product gas that has had methane removed from it, the reactor will produce more methane per pound of feedstock and the methane will be of higher quality, i.e., it will contain less carbon dioxide and have a higher BTU rating. In a preferred embodiment, a gas recirculator will comprise a sparger bar for adding a methane-stripped or reduced product gas, such as $CO_2$, back into the anaerobic digester, an inlet port for receiving gas from the anaerobic digester, and one or more pumps and/or gas separators.

Another preferred embodiment of the invention provides an anaerobic digester system comprising a gas recirculation system comprising a gas separator for removing methane from the discharge gas received directly or indirectly from the anaerobic digester to form a methane-reduced gas, or carbon dioxide enriched gas, which is subsequently fed directly or indirectly back into the anaerobic digester. In this manner, the thermodynamic equilibrium for the digestion of the feedstock is pushed toward methane production and carbon dioxide consumption.

Another preferred sparger bar will recirculate gas from the headspace of the reactor back through the reaction solution and preferably the sludge layer to improve conversion of carbon dioxide to methane.

A fluid recirculator will preferably recirculate reaction solution from a first part of the reaction vessel to a second part of the reaction vessel. Alternatively, the fluid recirculator will recirculate feedstock slurry, scum sludge, supernatant or reaction effluent, or portions thereof through the reaction vessel. For example, the recirculator could recirculate either one or more of the scum, supernatant or sludge phases of the reaction effluent. A recirculator could also recirculate one or more fluids removed from the digester and added to a tank back to the digester. A recirculator could also recycle supernatant into the feedstock feeder to aid in preparing the feedstock slurry. According to another preferred embodiment, a fluid that is recycled back into the reaction vessel will have been stripped of at least some and preferably most or all of its methane gas prior to being added back to the reaction vessel.

Mechanical agitators which are useful in the anaerobic digester include all known fluid agitators such as a turbine, propeller, impeller, paddle, wheel, helical bar, stirrer, rotating reaction vessel, flexible tube or rod, magnetic agitator, tumbler, paddle wheel, and other mechanical agitators known to those of ordinary skill in the art of fluid mixing. The preferred mechanical agitator is a paddle.

By operating the anaerobic digester at higher pressures, higher quality, i.e., purer, methane is produced. Generally, the higher the digester pressure, the higher the purity or BTU rating of methane produced by the reaction vessel. The anaerobic digester generally does not require pressurization by external means as gas formation in the digester tends to pressurize the reaction vessel sufficiently. However, the reaction vessel can be pressurized with a pressurizer. The pressurizer can be a compressed gas cylinder, pump, or other such equipment, that forces an inert gas, a produced gas, feedstock slurry, or reaction effluent into the reaction vessel to increase the pressure of the reaction vessel to the desired operating pressure. Accordingly, the feedstock slurry feeder, gas recirculator, fluid recirculator, sparger bar or combinations thereof can serve as the pressurizer. In a preferred embodiment, the anaerobic digester system will comprise one or more pressure relief valves, vents or exhaust valves to reduce pressure within the reaction vessel. The anaerobic digester will also preferably comprise a pressure controller capable of controlling pressure within the reaction vessel and/or a pressure monitor capable of monitoring pressure within the reaction vessel. The anaerobic digester system can also comprise one or more pressure gauges that indicate the pressure within the system.

The feedstock slurry feeder can be a force-feed or gravity-feed system; however, a force-feed system is preferred. Preferred feeders include pumps of all types or gas pressurized feed tubes or chambers. Pumps are generally more preferred and a progressive cavity pump is most preferred.

The productivity of the anaerobic digester system, in terms of gas, especially methane, production is related to the pressure within the reaction vessel. The present inventors have found that the anaerobic digester can be operated at pressures exceeding 10 psi up to a pressure that does not exceed the design operating pressure of the gas handling system or prevent methane gas from flashing out of the liquid slurry in the digester. The increased pressure effects an increase in the rate of gas, preferably methane, production and feedstock digestion thereby reducing digestion periods and increasing the overall productivity of the anaerobic digester system in terms of ft.$^3$ of methane produced per pound of feedstock. Generally, the higher the pressure of the reaction vessel headspace, the higher the BTU rating of the methane gas produced.

Temperature affects the productivity of the anaerobic digester. Generally, elevating the temperature will increase the productivity, e.g. faster or more efficient gas production, of the digester up to a temperature that is harmful to the microbial flora in the digester, at which temperature productivity will decrease. Different microbes have different optimal temperatures. The temperature of the reaction solution can be controlled with a temperature controller that heats and/or cools the reaction solution. The temperature controller can be a heater, heat exchanger, jacket surrounding the reaction vessel, coil within the reaction vessel or other such equipment used for controlling the temperature of fluids within reactors. The temperature of the reaction vessel will preferably be monitored with a temperature monitor, such as a thermocouple or other equipment known to those of ordinary skill in the art. Alternatively, the temperature of the reaction solution is controlled by adding a temperature controller to the fluid recirculator, the sparger bar, or the feedstock slurry feeder. A heating or cooling jacket surrounding the reaction vessel is alternatively used to control the temperature of the reaction vessel contents.

Fluid levels in the reaction vessel are monitored with a fluid level detector and controlled with a fluid level controller that either increases or decreases the flow of feedstock slurry into or reaction effluent out of the reaction vessel.

Figure 1B:
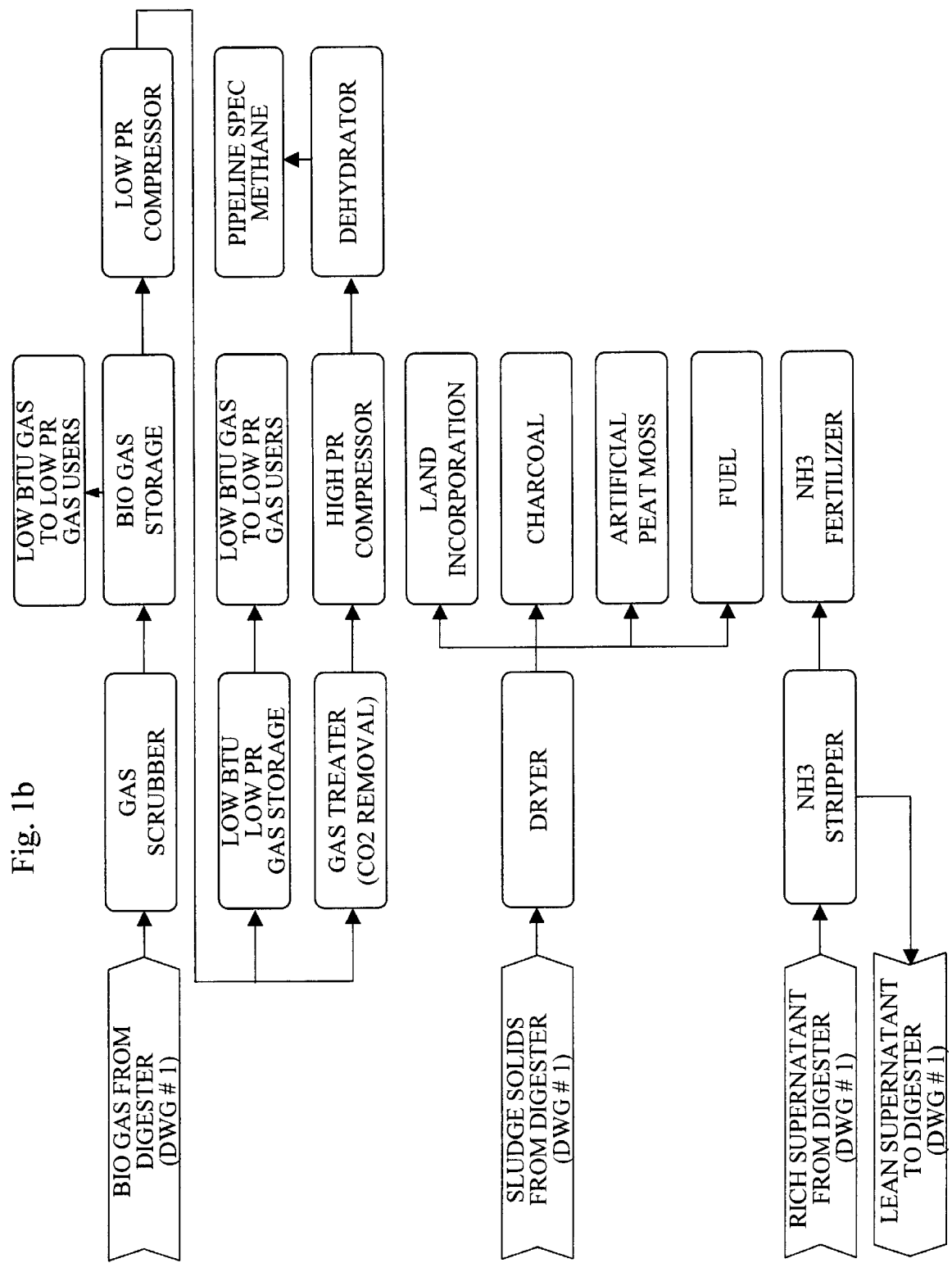

FIGS. 1a and 1b include a process flow schematic of a first embodiment of the anaerobic digester system according to the invention. In this embodiment, cotton burrs obtained from a cotton gin are converted to methane and a nutrient rich effluent. Cotton burrs are separated from raw cotton in a cotton gin. The processed cotton is baled and the cotton seed is collected. The cotton burrs are collected and sized in a grinder to an acceptable particle size to form a feedstock. The dirt and sand in the feedstock are separated from the cotton burrs in a cleaner. A calculated amount of cotton burrs and a calculated amount of chicken manure, which together provide a feed mixture having an approximately 30:1 carbon:nitrogen ratio, are placed in a slurry mixer and heated fresh water is added to form a feedstock slurry which is fed directly into the digester. An anaerobic microbe is added to the digester to form a reaction solution that is heated. In batch operation, the digestion period is allowed to extend for 1 to 60 days, preferably less than 45 days, and more preferably less than 30 days, while forming a biogas containing predominantly methane and carbon dioxide and possibly other gaseous compounds. The biogas is passed through a scrubber to remove unwanted components to form a raw gas mixture that is then passed through a low-pressure compressor. The raw gas mixture from the low-pressure compressor is collected in a low-pressure storage tank or passed through a gas treater to remove carbon dioxide from the raw gas and form high purity (>90% wt., or >95% wt., or >98% wt.) methane. The high purity methane is then compressed with a high-pressure compressor and dried with a dehydrator to form "sweet-dry" methane. The sludge from the anaerobic digester is sent to a collection tank or a dryer to form dried sludge that can be used as landfill, artificial peat moss, charcoal briquettes, fuel or other similar purpose. The supernatant or effluent from the anaerobic reactor contains ammonia and is sent to an ammonia stripper that removes the ammonia from the supernatant. The treated or ammonia-stripped supernatant is then fed back into the anaerobic digester and used to digest additional feedstock. The ammonia collected from the supernatant can be used to make a plant fertilizer. Alternatively, a diluted form of the ammonia rich supernatant is used as a fertilizer without removing the ammonia therefrom.

Solid briquettes can be formed from the sludge by a process including the steps of: a) removing the sludge from the digester; b) optionally filtering the sludge in conventional solids filtration equipment to remove the excess fluid from the sludge to form a water-reduced sludge; c) forming the briquettes by pressure molding the water-reduced sludge; and d) optionally drying the briquettes in conventional drying equipment. Alternatively, the sludge can be dried after either step a) or step b) above. The briquettes and/or sludge need not be, but are preferably, completely dried before use as a fuel.

Figure 2:
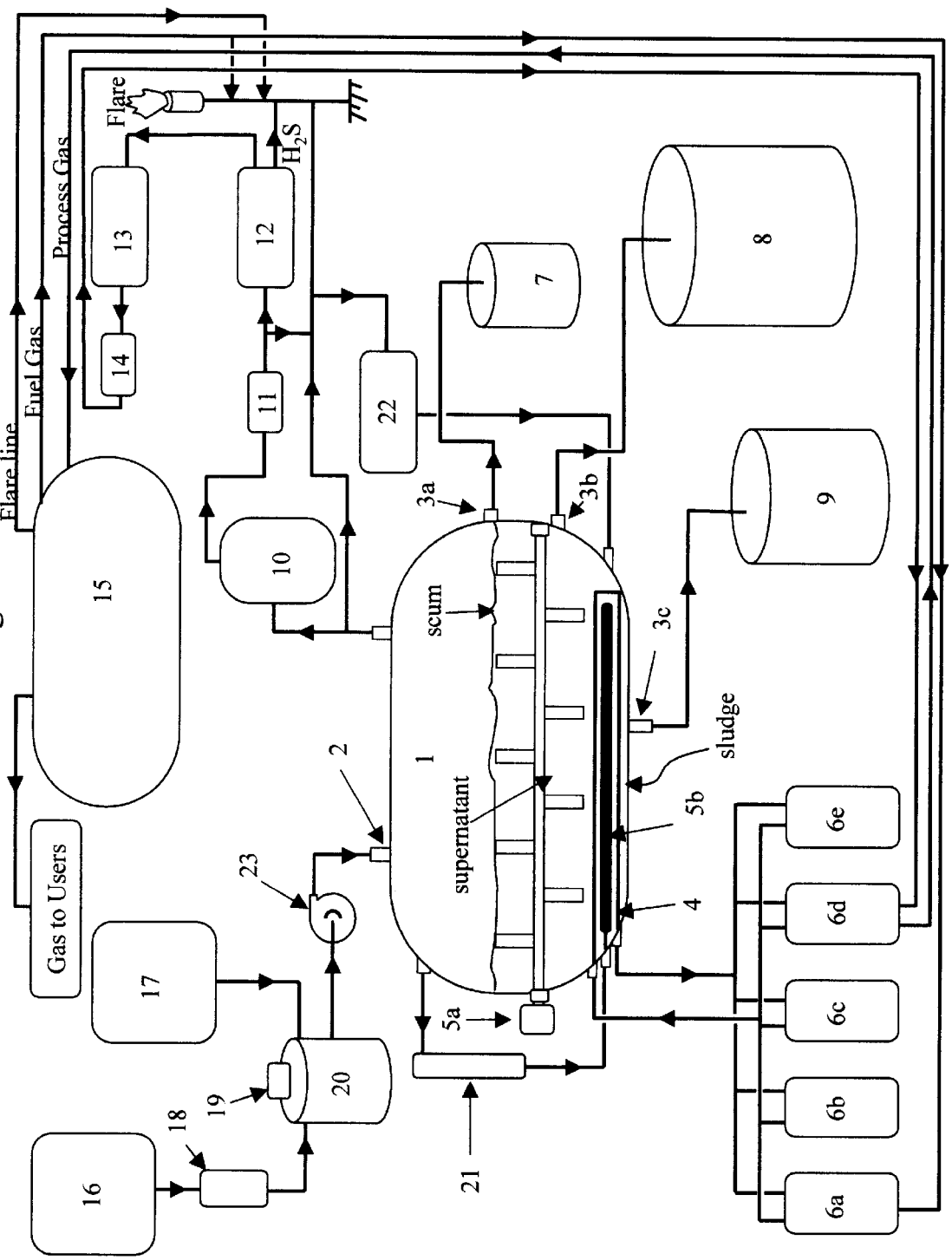
FIG. 2 is a process flow diagram of a second preferred embodiment of the anaerobic digester system of the invention.

FIG. 2 is a process flow diagram of a second preferred embodiment of the anaerobic digester system according to the invention comprising a feedstock source (16), a feedstock grinder (18), feedstock slurry tank (20) and mixer (19), a fresh water source (17), a gas-fired water heater (6a), a solar water heater (6b), a Jw/Dd-1 hot water heat exchanger (6c), an engine exhaust water heat exchanger (6e), a discharge-gas compressor/water heat exchanger (6d), a feedstock slurry feeder (23), an inlet port (2), an anaerobic digester (1), a reaction solution agitator (comprising a mechanical agitator (5a) and a sparger bar (5b)), effluent ports (3a-3c), a supernatant storage tank (8), a sludge storage tank (9), a scum storage tank (7), a discharge gas scrubber (10), a discharge gas compressor (11), a discharge gas treater (12), a gas treater outlet scrubber (13), a discharge gas aerial cooler (14) and a discharge gas storage vessel (15), a temperature controller coil (4), an optional low pressure biogas recirculator (21), and an optional high pressure biogas recirculator (22). The anaerobic digester (1) has a temperature controller, e.g. heating coil, (4) through which water from the heat exchangers or heaters is circulated to control the temperature of the reaction solution. A sparger bar (5b) in the anaerobic digester in combination with the low pressure gas recirculator (21) recirculates gas from the headspace through the reaction solution to provide mild agitation of the reaction solution. The mixer (5a) and the high pressure gas recirculator (22) provide more strenuous agitation if it is needed to mobilize the solids of the reaction solution.

Under standard operating conditions, a feedstock is loaded into the grinder (18) where it is ground to the desired particle size. The ground feedstock and an aqueous solution are then placed in tank (20) and mixed with the mixer (19) to form a feedstock slurry. An inoculate of an anaerobic microbe and an aqueous solution is loaded into the anaerobic digester (1). The feedstock slurry is loaded into the anaerobic digester (1) with the feeder (23) through the inlet port (2) until the desired amount of feedstock slurry is added. The digester contents are thoroughly mixed. The anaerobic digester is operated at an elevated pressure, such as that generated by the digester itself, and at a temperature sufficient to promote the digestion of the feedstock and the formation of the product gas. After a sufficient period of time has passed, the reaction solution is removed from the anaerobic digester as a whole, in portions, or from different parts of the digester. For example, if the reaction solution is permitted to partition in the digester, the reaction solution can be drawn from the scum, supernatant and/or sludge layers and placed in the respective tanks (7,8,9). The product gas is removed from the headspace of the digester (1) and passed through a gas scrubber (10). Once the product gas is removed from the digester, it is also termed the discharge gas. The discharge gas is then compressed by the gas compressor (11) and passed through the gas treater (12)—gas separation system (13) that removes $CO_2$, and $H_2S$ from the discharge gas. The $NH_3$ gas can be removed by passing the gas through a contactor and reboiler, regenerator and condenser, and a strong alkaline unit. The gases removed from the discharge gas can be passed through another gas separation system, not shown, that isolates one or more of the gas components. The gas separation system generally comprises a series of compressors, condensers, evaporators, pumps, tanks and optionally heating and/or cooling coils. The isolated component gas, preferably methane for burning or $CO_2$ for food grade $CO_2$ production, is then stored in the storage vessel (15) or released to a pipeline (not shown).

The supernatant, sludge and scum solutions and slurries, collectively termed the effluent, which are stored in their respective tanks (7,8,9), are then used as nitrogen rich fertilizer, insecticidal mixture, landfill, anaerobic digester inoculant, or other useful purpose. In addition, the effluent can be dried using conventional equipment to form valuable solid materials that can also be used as fertilizers, charcoal, carbon black, or other useful materials. The anaerobic digester tends to form ammonia, which can be removed from the product gas by the scrubber (10), gas treater (12) or gas separation system (13). The ammonia can be removed from the effluent by evaporation, condensation, precipitation or reaction with an acid source using methods well known in the art. The effluent can also be filtered, centrifuged or placed in settling tanks to separate the solids from the aqueous solution portion.

The product gas, if methane, can be used to operate gas-powered machinery such as the hot water heat exchanger (6d), the water heater (6a), and other equipment detailed above. Accordingly, the anaerobic digester system of the invention can be used in a ranch or farm setting to form a self-sustaining system. For example, the anaerobic digester system can be operated in conjunction with a chicken (broiler/hens) house to convert waste from the chicken house to methane gas, which is used to operate machinery or equipment associated with the chicken house. A cooperative system as described will in effect permit significant waste reduction thereby reducing the harmful effects that excessive hen house waste has on the environment. According to another example, the anaerobic digester system of the invention is used cooperatively in conjunction with a swine ranch to convert swine waste to methane and a fertilizer solution, wherein the methane is used to operate machinery used in the swine ranch. Other examples include the use of the anaerobic digester system in a cattle feedlot or a dairy cattle operation to convert waste material to methane and an insecticidal solution, wherein the methane is used to operate machinery used in the feedlot or dairy ranch.

The anaerobic digester can be operated such that the reaction solution is well mixed or stratified into the scum, supernatant and sludge zones or layers. When stratified, the scum layer includes materials that float in the reaction solution or are not well digested by the anaerobic microbe in the digester. The sludge layer includes materials that are denser than water and may or may not be digested by the anaerobic microbe. The sludge can also include feedstock solids that have not yet been digested. The supernatant layer is between the scum and sludge layers and generally comprises the bulk of the reaction solution. The supernatant layer includes water soluble components of the feedstock slurry and water soluble components, such as organic acids and ammonia, produced by the anaerobic microbe or other microbe or enzyme catalyst present in the digester.

The anaerobic digester system of the invention can be used to digest feedstock comprising any farm plant waste or any farm animal manure mixed with the proper additives to maintain an approximately 30:1 carbon:nitrogen ratio. Exemplary feedstock include cotton burrs; cow manure; cow manure mixed with feed, straw, hay, alfalfa, grass, soil, sand, tumble weeds and/or wood shavings; and chicken manure and urine containing wood shavings or cotton burrs. The useful materials prepared with these feedstock materials include ammonia, methane, charcoal (briquettes), carbon black, carbon dioxide, a nitrogen rich fertilizer, an insecticidal solution, and/or an insect repellant.

The supernatant solution taken directly from the reactor was tested as an insecticidal solution. The supernatant was applied directly to active fire ant mounds in a lawn. Within 24–48 hours, the ant mounds were inactive. In some cases, no ant activity has been seen in the treated mounds for a period of up to three to five months. The surrounding treated lawn is lush and thriving.

Methane was prepared in the anaerobic digester system exemplified herein. The product gas was collected from the headspace of the digester and passed through a scrubber containing a mist pad, or a glycol solution. The product gas was then compressed to about 300 psi. The gas was then passed through an amine gas treater to remove $CO_2$. The gas was then pressurized above 300 psi and passed through a dehydrator to remove water to form sweet dry methane. Finally, the methane was stored in a pressurized vessel for later use.

Each of the sludge or supernatant layers prepared with the anaerobic digester served as a nitrogen enriched fertilizer. For example, an effluent solution that had been 80–90% digested was applied to grass at the required rate. The effluent could be diluted with water prior to application. Water containing effluent was applied to a nearby patch of grass. Within about one to four weeks, the treated grass was visibly greener and lusher than nearby untreated grass.

Carbon dioxide is a common product of anaerobic digestion. The carbon dioxide could be separated from the methane by use of a gas treater. The isolated carbon dioxide can be used to make dry ice, to pressurize the anaerobic digester or to provide an inert atmosphere in the anaerobic digester. Alternatively, the carbon dioxide can be reacted with caustic in the presence of heat or a catalyst to form a bicarbonate salt. The carbon dioxide can also be fed back into the digester to be converted to methane and increase the overall yield of bioconversion to methane.

Ammonia is also a common product of anaerobic digestion. The ammonia can be separated from the carbon dioxide and methane by using a gas separator. The ammonia can be isolated as liquid, compressed gas, or aqueous solution containing ammonia. For example, when the product gas is treated with water in the scrubber in a countercurrent manner, the water absorbs the ammonia from the product gas thereby generating an aqueous solution containing ammonia. Alternatively, the ammonia can be separated from the other gases by treating the product gas with an acidic agent that reacts with ammonia to form an ammonium salt or by passing the product gas through a bed containing a sequestrant of ammonia to sequester the ammonia. The ammonia can be used to make fertilizer or other nitrogen-based products.

The sludge and scum layers contain relatively high concentrations of solids. When the solids are dried, they can be used in fertilizer, ground fill, pressed board material, solid fuel, pressed fireplace logs, charcoal briquettes, medium for water filters, or as a "peat moss" equivalent. Alternatively, the sludge and scum layers removed from the reactor can be added back to the reactor. The solids may also be pulverized into a dust and blown into a burner system for a boiler or furnace for use as a fuel. The sludge can be dried by air, sun, and/or heat.

Figure 4:
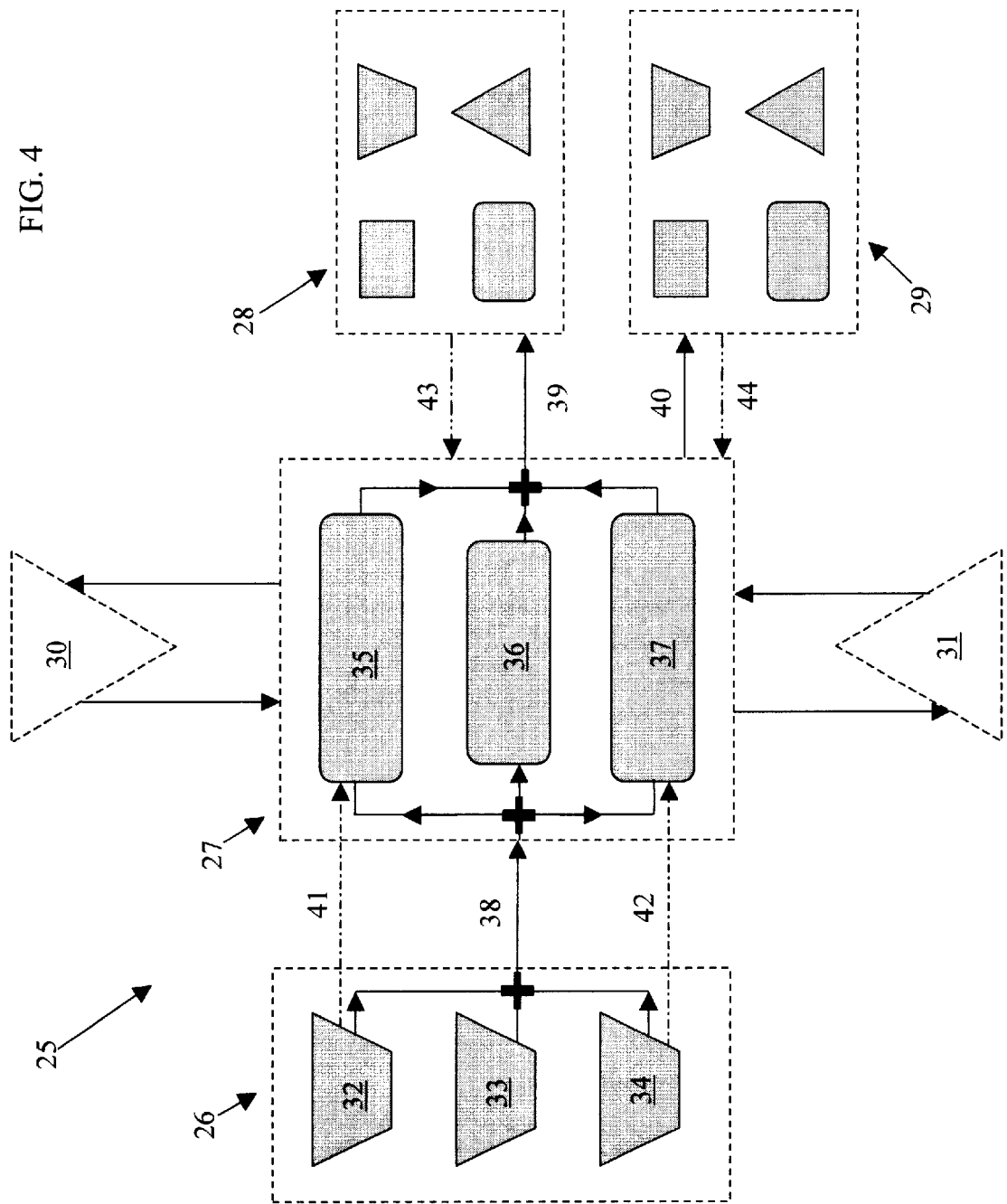
FIG. 4 depicts a process flow diagram of a third embodiment of the anaerobic digester system, wherein the system comprises two or more pressurizable anaerobic digesters connected in parallel.

FIG. 4 depicts one embodiment of an integrated anaerobic digester system (25) comprising a feedstock slurry feeder system (26), a single-stage anaerobic digester system (27), a discharge gas processing system (29), an enriched effluent processing system (28), a gas recirculation system (31), and an effluent recirculation system (30). The feeder system prepares the aqueous feedstock slurry in one or more vessels (32–34) and charges the feedstock into the anaerobic digester system (27). The vessels (32–34) are connected in parallel via the conduits (38) or each vessel can be connected to a corresponding anaerobic digester (35–37, respectively) via the conduits (41–42). The anaerobic digester system (27) comprises three anaerobic digesters (35–37) connected in parallel, such that the effluent of one digester does not enter another digester by way of the conduits (38) or (39). The flow of mass is indicated by the direction of the arrows. Together, the three anaerobic digesters (35–37) represent a single stage of anaerobic digestion, meaning that the feedstock is converted to discharge gas and enriched effluent without having to go from a first anaerobic digester (35) into a second anaerobic digester (36). This is unlike the system of Ort, which requires that the feedstock be predigested in a first anaerobic digested and then completely digested in a second anaerobic digester; therefore, the anaerobic digesters of Ort are connected serially as opposed to being in parallel.

Even though the anaerobic digester system (27) is depicted with three anaerobic digester vessels (35–37) it can comprise two, four or more such vessels. The vessels can be of the same construction and design or they can be different. In other words, each anaerobic digester vessel within a system can be the same or different than another digester vessel in the same system.

After digestion has progressed to the desired extent, the effluent is passed onto the effluent processing system (28) by way of the conduit (39). There it is processed as described previously herein. The effluent processing system comprises the above-described components. The effluent processing system (28) can be used as an effluent recirculation system (as indicated by the dash-dot-dot arrow (43)), wherein effluent is returned to the same anaerobic digester from which it is taken. Alternatively, a separate effluent recirculation system (30) can be used. In either case, effluent is returned to the same anaerobic digester from which it is taken.

The discharge gas is passed onto the discharge gas processing system (29) by way of the conduit (40), where it is processed as described previously herein. The discharge gas processing system comprises the above-described components. The discharge gas processing system can be used as a gas recirculation system (as indicated by the dash-dot-dot arrow (44)). Alternatively, a separate gas recirculation system (31) can be used.

The integrated system can also comprise a pressurizer system (not shown in FIG. 4) that pressurizes the anaerobic digester vessels (35–37). The pressurizer system will comprise the above-described components.

The connection of the various systems (26–31) of the integrated system (25) permits ease of total system and individual system scaling such that each system and the system as a whole can be scaled as needed. For large scale production, for example, the feeder system could comprise two mixing vessels; the digester system could comprise four digesters; and the entire system could comprise one or more of each an effluent recirculation system, a discharge gas recirculation system, a discharge gas processing system and an enriched effluent processing system. For small scale production, for example, the feeder system would comprise one mixing vessel; the digester system would comprise one digester; and the entire system could comprise one of each an effluent recirculation system, a discharge gas recirculation system, a discharge gas processing system and an enriched effluent processing system.

The carbon to nitrogen ratio of the non-water components of the feedstock will affect the performance of the digester, i.e., it will affect the productivity of the system, the efficiency of the digestion, the conversion of carbon dioxide to methane, the ability to maintain a stable pH and operating temperature. Generally, the carbon to nitrogen ratio of the feedstock will be about 30:1 for the systems exemplified below; however, feedstock having a carbon to nitrogen ratio in the range of about 25:1 to about 35:1 will still provide suitable results. When the carbon:nitrogen ratio of the feedstock is too high, the digestion will be less efficient and will leave an amount of undigested cellulose material.

For feedstock material having a low nitrogen content, a suitable feedstock slurry is obtained by adding a high nitrogen content. As detailed in the examples herein, cotton burrs (low nitrogen content feedstock) is mixed with chicken manure (high nitrogen content material) to form a feedstock material having an approximately 31:1 carbon:nitrogen ratio. The ammonia stripped from the digester effluent or discharge gas can be added in salt, liquid or gas form to a low nitrogen containing feedstock in order to raise the nitrogen content of the feedstock before addition to the digester.

In order to maintain a relatively constant pH for the slurry being digested, it may be necessary to add a buffering agent, alkalizing agent or acidifying agent to the slurry.

As used herein, the term "buffering agent" is intended to mean a compound used to resist change in pH. Such compounds include, by way of example and without limitation, potassium metaphosphate, potassium phosphate, monobasic sodium acetate and sodium citrate anhydrous and dihydrate and other materials known to one of ordinary skill in the art.

Generally, an acidifying agent will not be needed as the digestion of the feedstock tends to generate organic acids that drop the pH of digestion medium. As used herein, the term "acidifying agent" is intended to mean a compound used to provide an acidic medium to counteract a rise in pH of the digestion medium. Such compounds include, by way of example and without limitation, inorganic acid, acetic acid, amino acid, citric acid, fumaric acid and other alpha hydroxy acids, such as hydrochloric acid, ascorbic acid, and nitric acid and others known to those of ordinary skill in the art.

Generally, an alkalizing agent will be required since digestion of the feedstock tends to generate organic acids that drop the pH of digestion medium. As used herein, the term "alkalizing agent" is intended to mean a compound used to provide alkaline medium to counteract a drop in pH of the digestion medium. Such compounds include, by way of example and without limitation, lime, lye, ammonia solution or gas, ammonium carbonate, potassium hydroxide, sodium borate, sodium carbonate, sodium bicarbonate, sodium hydroxide and others known to those of ordinary skill in the art.

When an anaerobic digester system is constructed according to the invention, loaded with the correct mixture of components in order to form a feedstock having the desired carbon to nitrogen ratio, operated at the desired pressure and temperature and pH, the system will produce high purity methane gas.

The anaerobic digester system can be used to purify impure methane gas containing carbon dioxide. In this instance, the impure gas is injected into the digester containing a digestion slurry. As the impure gas is added, the methane gas flashes through the digestion slurry while a portion or all of the carbon dioxide is absorbed by the digestion slurry. The absorbed carbon dioxide is then converted to methane such that ultimately higher purity methane gas is produced.

The following examples should not be considered exhaustive, but merely illustrative of only a few of the many embodiments contemplated by the present invention. The methods described herein can be followed to conduct anaerobic digestion according to the invention.

EXAMPLE 1

Anaerobic Digestion of Cotton Burrs Mixed with Chicken Manure

This process was conducted in a batch-type manner. Fresh well water (318 gal.) was loaded into a digester equipped with an internal mechanical agitator and a heat controller. The water was heated until it reached a temperature of about 100° F. Then, anaerobic bacterium inoculant (10 gal.) and fresh wet chicken manure (14.5 lbs.) were added to the water with mixing. Finally, clean unground cotton burrs (200 lbs.) were added to the digester with mixing and the digester was sealed. The digester was then purged repeatedly with nitrogen gas to create a substantially anaerobic environment. With this loading, the percent solids of the reaction solution was approximately 4.48%. The digester was run for a period of 45 days with periodic sampling of the headspace. The temperature ranged from about 95° F. to about 120° F. and averaged about 105° F. to about 110° F. The pressure within the digester ranged from about 1 psi to about 45 psi. The total amount of gas produced was about 931.5 ft.$^3$. The average rate of gas production was about 0.88 ft.$^3$/hr, about 0.004 ft.$^3$/hr/lb. of burrs or about 4.66 ft.$^3$/lb. of burrs. The individual gas components of the product gas ranged from about 49% wt. to about 65% wt. for methane and from about 51% wt. to about 35% wt. for carbon dioxide. The content of ammonia in the product gas was not measured.

The following analytical measures were determined for the cotton burrs and chicken manure used in this procedure.

| MEASURE | BURRS | CHICKEN MANURE | TOTAL | DRIED SOLIDS IN EFFLUENT |
|---|---|---|---|---|
| Carbon (lbs. | 16.0789 | 1.16 | 17.2389 | |
| Nitrogen (lbs.) | 0.429 | 0.1239 | 0.5529 | |
| Carbon/Nitrogen | 37.48 | 9.39 | 31.18 | |
| Energy (BTU/lbs.) | 7593 | 7330 | | |
| Ash (% wt.) | 6.00 | 10.91 | | 7.22 |
| Volatile Solids (% wt.) | 76.30 | 16.52 | | 69.33 |
| Moisture (% wt.) | 17.49 | 71.5 | | 23.45 |
| Nitrogen (% wt.) | 0.21 | 1.03 | | |

For other 200 lbs. batches using approximately the same amounts of ingredients, the total C/N ratio ranged from about 30 to about 32. In other batches run according to this procedure, the percent solids ranged from 4.5% to 5.0% wt.

EXAMPLE 2

Anaerobic Digestion of Cotton Burrs Mixed with Chicken Manure

This procedure was substantially the same as that of Example 1. The digester produced product gas containing about 63% methane.

EXAMPLE 3

Anaerobic Digestion of Cow Manure

Figure 3:
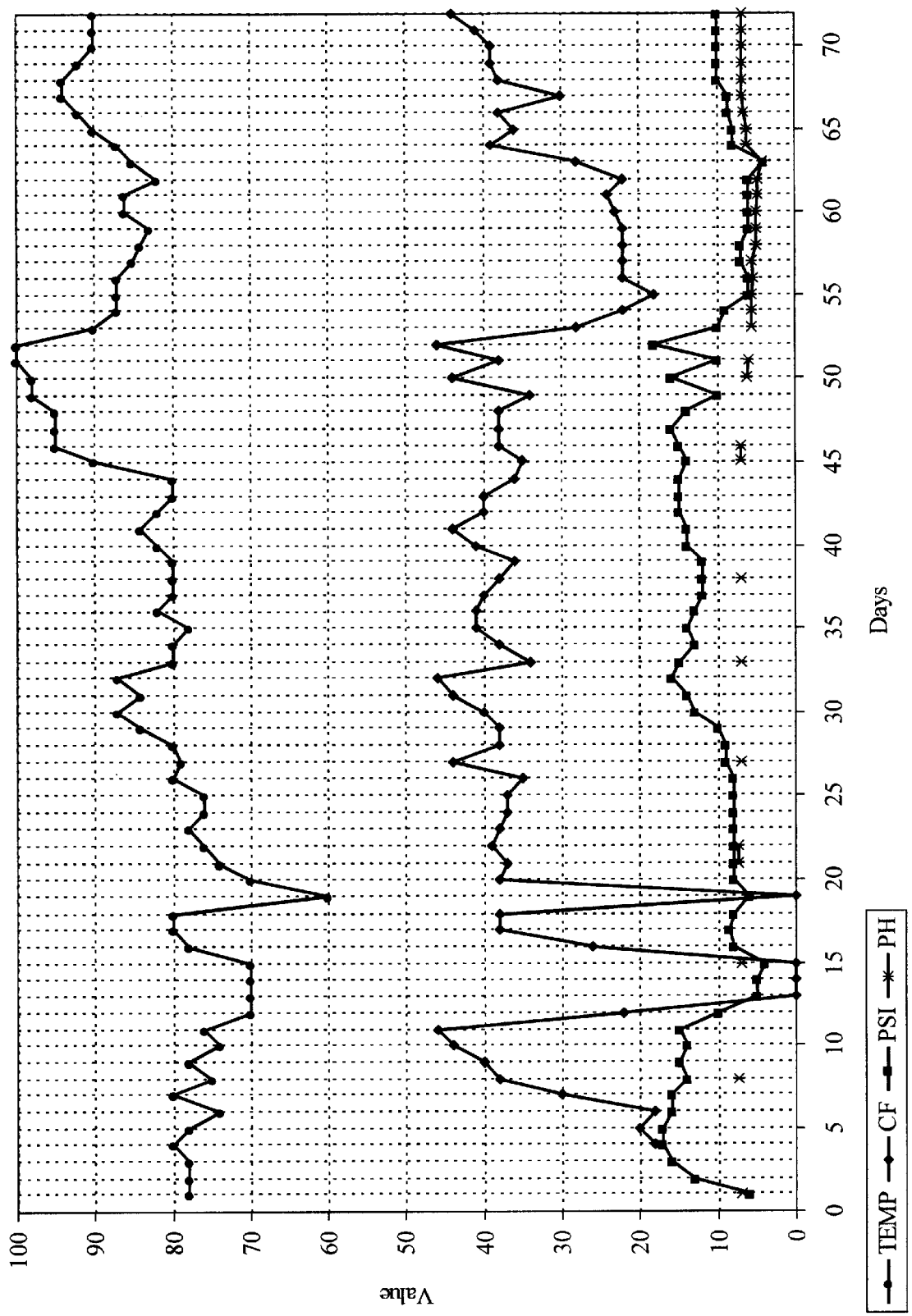
FIG. 3 is a chart depicting the temperature, pH, pressure and methane gas volume production of an exemplary digester according to the invention.

This process was conducted in a batch manner. Fresh well water (150 gal.) was loaded into a digester equipped with an internal mechanical agitator and a heat controller. The water was heated until it reached a temperature of about 100° F. Then, a Clostridium spp. inoculant (1 gal.) and cow manure slurry (60 gal.) were mixed in a vessel having a total capacity of 150 gal., added to the digester and the digester was sealed. The digester was then purged repeatedly with nitrogen gas to create a substantially anaerobic environment. With this loading, the percent solids of the reaction solution was approximately 25–50%. The pH of the digester slurry was optionally adjusted to about 6.5–6.8 with lime. The digester was run for a period of 80 days with periodic sampling of the headspace. The temperature ranged from about 70° F. to about 100° F. and averaged about 80° F. to about 85° F. The pressure within the digester ranged from about 5 psi to about 18 psi. The pH of the reaction solution was kept between about 6.5–6.8 by the addition of lime. The methane produced was vented each day and the amount collected ranged from about 20–40 ft.$^3$ and averaged about 30–40 ft.$^3$. The total amount of methane produced was about 2000 ft.$^3$. About 10–15 lbs. of feedstock were added on a semi-weekly basis. The total amount of feedstock added was about 300 lbs. The amount of sludge, scum and supernatant removed from the reactor was about equal to the amount of feedstock added. The average rate of gas production was about 6–7 ft.$^3$/hr of methane/lb. of feedstock. FIG. 3 depicts a chart of the measurements obtained for reaction solution pH, amount of methane gas produced (ft.$^3$), reaction solution temperature (° F.), and the headspace pressure of the reactor (psi). The BTU rating of the methane produced by the digester operated under these conditions ranged from about 600 to 850.

EXAMPLE 4

Anaerobic Digestion of Partially Composted Chicken Mixed with Cotton Gin Trash Compost material, obtained from a plant in Mt. Pleasant, Tex., contained 75% wt. chicken (feathers, blood, bone, organs, flesh, intestines) and 25% wt. gin trash. The compost material had been composted for four days in a rotating composter prior to placement in the anaerobic digester. The anaerobic digester was operated within the acceptable ranges of the operating parameters described herein. The anaerobic digester (55 gal. size drum) included an inoculant obtained from a previous digestion of chicken manure. The particle size of compost material fed into the anaerobic digester was about 1.5 inches initially and was reduced to less than 0.5 inches during the period of digestion. The composted material was slurried with water to a ratio of about 1 part water to 2 parts compost material prior to sealing the digester. Methane production began about four days after the digester was sealed. Methane gas was released from the digester daily. The anaerobic digester was operated for six weeks and produced methane gas at a rate as described herein.

A process as described herein can be conducted in a meat, in particular chicken, rendering plant.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

We claim:

1. A system for converting cellulose-containing feedstock into useful materials, wherein the system comprises:
    one or more feedstock slurry feeders;
    two or more pressurizable anaerobic digesters connected in parallel, each anaerobic digester comprising agitation means, one or more feed ports, one or more discharge ports, an optional pressure regulator, and a reaction vessel for holding a reaction solution comprising an anaerobic microbe which converts an aqueous slurry of cellulose-containing feedstock into at least methane and an enriched effluent;
    one or more pressurizers;
    one or more gas processors directly or indirectly connected to each anaerobic digester; and
    a plurality of conduits connecting various components of the system;
    wherein the headspace of each anaerobic digester is pressurizable to about 10 psi or more to form the enriched effluent and a discharge gas comprising at least methane during anaerobic digestion of the feedstock slurry.

2. The system of claim 1 further comprising one or more of the following:
    a) one or more pressure controllers for controlling the pressure inside the anaerobic digesters; and
    b) one or more temperature controllers for controlling the temperature inside the anaerobic digesters.

3. The system of claim 2, wherein at least one of the one or more pressure controllers comprises an actuator for the pressurizer and a pressure monitor.

4. The system of claim 2, wherein at least one of the one or more temperature controllers is selected from a coil inside the anaerobic digester, a jacket outside the reaction vessel, and a combination thereof.

5. The system of claim 4, wherein at least one of the one or more temperature controllers further comprises a recirculating fluid source outside the reaction vessel.

6. The system of claim 5, wherein the recirculating fluid source is selected from the group consisting of a solar water heater, a gas-powered water heater, a steam generator, and a heat exchanger.

7. The system of claim 1 further comprising one or more vessels for preparing a feedstock slurry.

8. The system of claim 1 further comprising a feedstock particle size reducer.

9. The system of claim 1 further comprising one or more storage tanks for receiving the enriched effluent.

10. The system of claim 9, wherein the one or more storage tanks is independently selected at each occurrence from the group consisting of a scum storage tank, a supernatant storage tank and a sludge storage tank.

11. The system of claim 1, wherein the one or more gas processors is selected from the group consisting of a gas scrubber, a gas compressor, a gas separator, a gas treater, and an aerial cooler.

12. The system of claim 1, wherein the agitation means is selected from the group consisting of a fluid recirculator, a gas recirculator, a sparger bar, a mechanical agitator and a combination thereof.

13. The system of claim 1, wherein the pressurizer is one or more of the feedstock slurry feeder; an external compressed gas source; a fluid inlet; a sparger bar; a gas recirculator; and a fluid recirculator.

14. The system of claim 1, wherein the at least one useful gas is selected from the group consisting of methane, ammonia, hydrogen, hydrogen sulfide and carbon dioxide.

15. The system of claim 1, wherein the enriched effluent comprises at least one of a nitrogen rich fertilizer, an insecticidal mixture, ammonia, and an organic acid.

16. The system of claim 1, wherein the system forms at least one useful material selected from the group consisting of methane, ammonia, hydrogen, hydrogen sulfide, carbon dioxide, a nitrogen rich fertilizer, an insecticidal mixture, and an organic acid.

17. The system of claim 1 further comprising a gas recirculation system comprising a gas separator for reducing methane from a discharge gas received directly or indirectly from an anaerobic digester to form a methane-reduced gas that is subsequently fed directly or indirectly back into the anaerobic digester.

18. The system of claim 1 further comprising a fluid recirculation system for recirculating scum, sludge, supernatant or effluent received directly or indirectly from an anaerobic digester back into the anaerobic digester.

19. The system of claim 1, wherein the configuration of the anaerobic digester system permits batch, semi-continuous or continuous operation.

20. The system of claim 19, wherein the agitation means comprises a gas bubbler, an aerator, a sparger bar, a fluid stream, a mechanical agitator, or a combination thereof.

21. The system of claim 1, wherein the anaerobic digesters comprise an anaerobic microbe which is a methanogenic bacterium.

22. The system of claim 21, wherein the anaerobic microbe is mesophilic or thermophilic.

23. The system of claim 1, wherein the feedstock slurry comprises from about 1% wt. to about 90% wt. solids.

24. The system of claim 1 further comprising at least one of an internal combustion engine, an electrical current generator, an electric engine, a water heater, a furnace, an air conditioning unit, a ventilation fan, a conveyor, a pump, a heat exchanger, and a fuel cell.

25. The system of claim 24, wherein the at least one useful gas is used to operate at least one of the internal combustion engine, electrical current generator, electric engine, water heater, furnace, air conditioning unit, ventilation fan, conveyor, pump, heat exchanger, and fuel cell.

26. The system of claim 1, wherein the anaerobic digesters comprise an anaerobic microbe selected from the group consisting of:

Clostridium spp., Bacillus spp., Escherichia spp., Staphylococcus spp., Methanobacter spp., *Methanobacter (Mb.) omlianskii, Mb. formicicum, Mb. soehngenii, Mb. thermoautrophicum, Mb. ruminatium, Mb. mobile, Mb. methanica, Methanococcus (Mc.) mazei, Mc. vannielii, Ms. mazei, Mb. suboxydans, Mb. propionicum, Methanosarcina (Ms.) bovekeri, Ms. methanica, Ms. Alcaliphilum, Ms. acetivorans, Ms. thermophilia, Ms. barkeri, Ms. vacuolata, Propionibacterium acidipropionici, Saccharomyces cerevisae, S. ellipsoideus, Clostridium propionicum, Clostridium saccharoacetoper-butylicum*, and *Clostridium butyricum*.

27. The system of claim 26, wherein the at least one useful gas is selected from the group consisting of:

methane, hydrogen, carbon dioxide, hydrogen sulfide, and ammonia.

28. The system of claim 1, wherein the enriched effluent comprises at least one of ammonia; nitrogen rich fertilizer; protein; amino acid; carbohydrate; insecticide; mineral; charcoal; carbon black; and insect repellant.

29. The system of claim 1, wherein the anaerobic digesters comprise an aqueous slurry of cellulose-containing feedstock comprising at least one of animal tissue, biomass, fish tissue, plant parts, fruits, vegetables, plant-processing waste, animal-processing waste, animal manure, animal urine, mammalian manure, mammalian urine, solids isolated from fermentation cultures, bovine manure or urine, poultry manure or urine, equine manure or urine, porcine manure or urine, wood shavings or chips, slops, mostos, shredded paper, cotton burrs, grain, chaff, seed shells, hay, alfalfa, grass, leaves, sea shells, seed pods, corn shucks, weeds, aquatic plants, algae, fungus, and combinations thereof.

30. The system of claim 1, wherein the system is installed in a swine ranch, chicken farm, cattle ranch, feedlot or dairy cattle milking facility to convert waste material into at least methane, which is used to operate one or more gas-powered machines.

31. The system of claim 1, wherein the system comprises a single feedstock slurry feeder connected to each of two or more pressurizable anaerobic digesters connected in parallel.

32. The system of claim 1, wherein the system further comprises one or more receiving tanks that receive the enriched effluent from each pressurizable anaerobic digester.

33. The system of claim 1 further comprising:

one or more vessels for preparing a feedstock slurry;

a feedstock particle size reducer;

one or more storage tanks for receiving the enriched effluent;

comprising a gas recirculation system for recirculating a gas received directly or indirectly from an anaerobic digester back into the anaerobic digester;

a fluid recirculation system for recirculating scum, sludge, supernatant or effluent received directly or indirectly from an anaerobic digester back into the anaerobic digester; and at least one of an internal combustion engine, an electrical current generator, an electric engine, a water heater, a furnace, an air conditioning unit, a ventilation fan, a conveyor, a pump, a heat exchanger, and a fuel cell.

34. An integrated system for converting cellulose-containing feedstock into useful materials, wherein the integrated system comprises:

a feedstock slurry feeder system that forms an aqueous slurry of cellulose-containing feedstock;

an anaerobic digester system directly or indirectly connected to the feeder system and comprising two or more pressurizable anaerobic digesters connected in parallel, wherein each anaerobic digester receives the aqueous slurry of cellulose-containing feedstock and converts it into a discharge gas and an enriched effluent; and a discharge gas processing system that is directly or indirectly connected to the anaerobic digester system and that at least separates methane from the discharge gas; wherein the headspace of each anaerobic digester is pressurizable to about 10 psi or more to form the enriched effluent and a discharge gas comprising at least methane during anaerobic digestion of the feedstock slurry.

35. The integrated system of claim 34 further comprising an enriched effluent processing system.

36. The integrated system of claim 35, wherein the enriched effluent processing system comprises one or more storage tanks for receiving the enriched effluent.

37. The integrated system of claim 36, wherein the one or more storage tanks is independently selected at each occurrence from the group consisting of a scum storage tank, a supernatant storage tank and a sludge storage tank.

38. The integrated system of claim 35 further comprising a pressurizer system.

39. The integrated system of claim 38, wherein the pressurizer is one or more of a feedstock slurry feeder, an external compressed gas source, a fluid inlet, a sparger bar, a gas recirculator, and a fluid recirculator.

40. The integrated system of claim 35, wherein the feedstock slurry feeder system comprises one or more mixing vessels and one or more pumps.

41. The integrated system of claim 40, wherein the feedstock slurry feeder system further comprises a feedstock particle size reducer.

42. The integrated system of claim 35, wherein the anaerobic digester is adapted for batch, semi-continuous or continuous operation.

43. The integrated system of claim 35 further comprising at least one component powered by methane produced by the integrated system, wherein the component is independently selected at each occurrence from the group consisting of an internal combustion engine, an electrical current generator, an electric engine, a water heater, a furnace, an air conditioning unit, a ventilation fan, a conveyor, a pump, a heat exchanger, and a fuel cell.

44. The integrated system of claim 35, wherein the discharge gas processing system comprises a dehydrator, separator, scrubber, compressor, treater and/or aerial cooler.

45. The integrated system of claim 44, wherein the separator separates $CO_2$ or ammonia gas from the discharge gas.

46. The integrated system of claim 35, wherein each anaerobic digester comprises agitation means, one or more feed ports, one or more discharge ports, an optional pressure regulator, and a reaction vessel.

47. The integrated system of claim 46, wherein the agitation means is independently selected a each occurrence from the group consisting of a fluid recirculator, a gas recirculator, a sparger bar, a mechanical agitator and a combination thereof.

48. The integrated system of claim 35 further comprising a gas recirculation system to recirculate gas from the headspace of an anaerobic digester to the slurry of the digester.

49. The integrated system of claim 48, wherein the gas recirculation system adds methane-depleted or carbon dioxide enriched discharge gas back to the anaerobic digester.

50. The integrated system of claim 35 further comprising a fluid recirculator system that recycles the scum, supernatant, effluent, or sludge of an anaerobic digester.

51. An integrated anaerobic digester system comprising:
a single-stage anaerobic digester system comprising two or more pressurizable anaerobic digesters connected in parallel, wherein each anaerobic digester receives an aqueous slurry of cellulose-containing feedstock and converts it into a discharge gas and an enriched effluent;
a discharge gas processing system that is directly or indirectly connected to the anaerobic digester system and that at least separates methane from the discharge gas; and
an enriched effluent processing system that is directly or indirectly connected to the anaerobic digester system;
wherein the headspace of each anaerobic digester is pressurizable to about 10 psi or more to form the enriched effluent and a discharge gas comprising at least methane during anaerobic digestion of the aqueous slurry of cellulose-containing feedstock.

52. The integrated system of claim 51 further comprising a feedstock slurry feeder system that forms an aqueous slurry of cellulose-containing feedstock.

53. The integrated system of claim 52, the feedstock slurry feeder system comprises one or more mixing vessels and one or more pumps.

54. The integrated system of claim 53, wherein the feedstock slurry feeder system further comprises a feedstock particle size reducer.

55. The integrated system of claim 52 further comprising a pressurizer system.

56. The integrated system of claim 55, wherein the pressurizer is one or more of a feedstock slurry feeder, an external compressed gas source, a fluid inlet, a sparger bar, a gas recirculator, and a fluid recirculator.

57. The integrated system of claim 52 further comprising a gas recirculation system that recirculates gas from the headspace of an anaerobic digester to the slurry of the digester.

58. The integrated system of claim 52 further comprising a fluid recirculation system that circulates the scum, supernatant, effluent, or sludge of an anaerobic digester within the digester.

59. The integrated system of claim 51, wherein the enriched effluent processing system comprises one or more storage tanks for receiving the enriched effluent.

60. The integrated system of claim 59, wherein the one or more storage tanks is independently selected at each occurrence from the group consisting of a scum storage tank, a supernatant storage tank and a sludge storage tank.

61. The integrated system of claim 51, wherein the anaerobic digester is adapted for batch, semi-continuous or continuous operation.

62. The integrated system of claim 52 further comprising at least one component powered by methane produced by the integrated system, wherein the component is independently selected at each occurrence from the group consisting of an internal combustion engine, an electrical current generator, an electric engine, a water heater, a furnace, an air conditioning unit, a ventilation fan, a conveyor, a pump, a heat exchanger, and a fuel cell.

63. The integrated system of claim 51, wherein the discharge gas processing system comprises a dehydrator, separator, scrubber, compressor, treater and/or aerial cooler.

64. The integrated system of claim 63, wherein the separator separates $CO_2$ or ammonia gas from the discharge gas.

65. The integrated system of claim 52, each anaerobic digester comprises agitation means, one or more feed ports, one or more discharge ports, an optional pressure regulator, and a reaction vessel.

66. The integrated system of claim 65, wherein the agitation means is independently selected a each occurrence from the group consisting of a fluid recirculator, a gas recirculator, a sparger bar, a mechanical agitator and a combination thereof.

67. An integrated anaerobic digester system comprising:
a single-stage anaerobic digester system comprising two or more pressurizable anaerobic digesters connected in parallel, wherein each anaerobic digester receives an aqueous slurry of cellulose-containing feedstock and converts it into a discharge gas and an enriched effluent;
a discharge gas processing system that is directly or indirectly connected to the anaerobic digester system and that at least separates methane from the discharge gas;
an enriched effluent processing system that is directly or indirectly connected to the anaerobic digester system;
a feedstock slurry feeder system that forms an aqueous slurry of cellulose-containing feedstock;
a pressurizer system;
a gas recirculation system that recirculates gas from the headspace of an anaerobic digester to the slurry of the digester; and
a fluid recirculation system that recirculates the scum, supernatant, effluent, or sludge of an anaerobic digester;
wherein the headspace of each anaerobic digester is pressurizable to about 10 psi or more to form the enriched effluent and a discharge gas comprising at least methane during anaerobic digestion of the aqueous slurry of cellulose-containing feedstock.

68. The integrated system of claim 67, wherein the enriched effluent processing system comprises one or more storage tanks for receiving the enriched effluent.

69. The integrated system of claim 68, wherein the one or more storage tanks is independently selected at each occurrence from the group consisting of a scum storage tank, a supernatant storage tank and a sludge storage tank.

70. The integrated system of claim 67, wherein the pressurizer is one or more of a feedstock slurry feeder, an external compressed gas source, a fluid inlet, a sparger bar, a gas recirculator, and a fluid recirculator.

71. The integrated system of claim 67, wherein the feedstock slurry feeder system comprises one or more mixing vessels and one or more pumps.

72. The integrated system of claim 71, wherein the feedstock slurry feeder system further comprises a feedstock particle size reducer.

73. The integrated system of claim 67, wherein the anaerobic digester is adapted for batch, semi-continuous or continuous operation.

74. The integrated system of claim 67 further comprising at least one component powered by methane produced by the integrated system, wherein the component is independently selected at each occurrence from the group consisting of an internal combustion engine, an electrical current generator, an electric engine, a water heater, a furnace, an air conditioning unit, a ventilation fan, a conveyor, a pump, a heat exchanger, and a fuel cell.

75. The integrated system of claim 67, wherein the discharge gas processing system comprises a dehydrator, separator, scrubber, compressor, treater and/or aerial cooler.

76. The integrated system of claim 75, wherein the separator separates $CO_2$ or ammonia gas from the discharge gas.

77. The integrated system of claim 67, each anaerobic digester comprises agitation means, one or more feed ports, one or more discharge ports, an optional pressure regulator, and a reaction vessel.

78. The integrated system of claim 77, wherein the agitation means is independently selected a each occurrence from the group consisting of a fluid recirculator, a gas recirculator, a sparger bar, a mechanical agitator and a combination thereof.

79. The integrated system of claim 67, wherein the gas recirculation system adds methane-depleted or carbon dioxide enriched discharge gas back to the anaerobic digester.

* * * * *